(12) United States Patent
Furnish et al.

(10) Patent No.: US 6,949,072 B2
(45) Date of Patent: Sep. 27, 2005

(54) DEVICES FOR VULNERABLE PLAQUE DETECTION

(75) Inventors: Simon Furnish, New York, NY (US); Jay Caplan, Belmont, MA (US); Andres Zuluaga, Boston, MA (US); Daniel E. McNulty, Winchester, MA (US)

(73) Assignee: InfraReDx, Inc., Cambridge, MA (US)

( * ) Notice: Subject to any disclaimer, the term of this patent is extended or adjusted under 35 U.S.C. 154(b) by 0 days.

(21) Appl. No.: 10/668,012

(22) Filed: Sep. 22, 2003

(65) Prior Publication Data

US 2005/0075574 A1 Apr. 7, 2005

(51) Int. Cl.⁷ .............................................. A61B 8/12
(52) U.S. Cl. ..................................................... 600/466
(58) Field of Search ............................... 600/459–471, 600/473–474, 549

(56) References Cited

U.S. PATENT DOCUMENTS

| | | | |
|---|---|---|---|
| 4,375,818 A | * 3/1983 | Suwaki et al. ............... 600/463 |
| 4,504,727 A | * 3/1985 | Melcher et al. ........ 219/121.62 |
| 4,794,931 A | 1/1989 | Yock |
| 5,029,588 A | 7/1991 | Yock et al. |
| 5,167,233 A | * 12/1992 | Eberle et al. ............... 600/470 |
| 5,576,013 A | 11/1996 | Williams et al. |
| 5,681,277 A | * 10/1997 | Edwards et al. ............... 604/22 |
| 5,716,595 A | 2/1998 | Goldenberg |
| 5,725,494 A | 3/1998 | Brisken |
| 5,728,092 A | 3/1998 | Doiron et al. |
| 5,916,210 A | * 6/1999 | Winston ......................... 606/7 |
| 5,924,997 A | * 7/1999 | Campbell .................... 600/549 |
| 5,935,075 A | * 8/1999 | Casscells et al. ........... 600/474 |
| 5,964,727 A | * 10/1999 | Edwards et al. ............... 604/22 |
| 6,016,440 A | 1/2000 | Simon et al. |
| 6,022,309 A | * 2/2000 | Celliers et al. ................. 600/7 |
| 6,054,449 A | 4/2000 | Robinson et al. |
| 6,134,003 A | * 10/2000 | Tearney et al. ............. 356/450 |
| 6,210,393 B1 | 4/2001 | Brisken |
| 6,296,619 B1 | 10/2001 | Brisken et al. |
| 6,615,071 B1 | * 9/2003 | Casscells et al. ........... 600/474 |
| 6,690,958 B1 | 2/2004 | Walker et al. |
| 6,692,430 B2 | * 2/2004 | Adler ......................... 600/109 |
| 6,701,181 B2 | * 3/2004 | Tang et al. .................. 600/478 |
| 2003/0028114 A1 | 2/2003 | Casscells, III et al. |
| 2003/0199767 A1 | 10/2003 | Cespedes et al. |
| 2003/0236443 A1 | 12/2003 | Cespedes et al. |

FOREIGN PATENT DOCUMENTS

WO    WO 90/13253    * 11/1990

OTHER PUBLICATIONS de Korte et al., "IVUS Elastography: In Vivo Validation", http://www.eur.nl/fgg/thorax/elasto/Invivo.html.
de Korte et al., "Identification of Atherosclerotic Plaque Components With Intravascular Ultrasound Elastography In Vivo: A Yucatan Pig Study", Circulation, 105:1627–1630, (Apr. 9, 2002).

* cited by examiner

*Primary Examiner*—Francis J. Jaworski
(74) *Attorney, Agent, or Firm*—Fish & Richardson P.C.

(57) ABSTRACT

An intravascular probe includes a sheath with a distal portion and a proximal portion. The intravascular probe includes a first optical waveguide extending along the sheath, the first optical waveguide being configured to carry optical radiation between the distal and proximal portions, and a first beam redirector disposed at the distal portion in optical communication with the first optical waveguide. The intravascular probe also includes an optical detector configured to receive optical radiation from the first optical waveguide, and an ultrasound transducer disposed at the distal portion. The ultrasound transducer is configured to couple ultrasound energy between the intravascular probe and a transmission medium. A wire extends along the sheath in electrical communication with the ultrasound transducer.

28 Claims, 8 Drawing Sheets

DEVICES FOR VULNERABLE PLAQUE DETECTION

TECHNICAL FIELD

The invention relates to devices for luminal diagnostics, and in particular, to devices for vulnerable plaque detection.

BACKGROUND

Atherosclerosis is a vascular disease characterized by a modification of the walls of blood-carrying vessels. Such modifications, when they occur at discrete locations or pockets of diseased vessels, are referred to as plaques. Certain types of plaques are associated with acute events such as stroke or myocardial infarction. These plaques are referred to as "vulnerable plaques." A vulnerable plaque typically includes a lipid-containing pool separated from the blood by a thin fibrous cap. In response to elevated intraluminal pressure or vasospasm, the fibrous cap can become disrupted, exposing the contents of the plaque to the flowing blood. The resulting thrombus can lead to ischemia or to the shedding of emboli.

One method of locating vulnerable plaque is to peer through the arterial wall with infrared light. To do so, one inserts a catheter through the lumen of the artery. The catheter includes a delivery fiber for illuminating a spot on the arterial wall with infrared light. A portion of the light penetrates the blood and arterial wall, scatters off structures within the wall and re-enters the lumen. This re-entrant light can be collected by a collection fiber within the catheter and subjected to spectroscopic analysis. This type of diffuse reflectance spectroscopy can be used to determine chemical composition of arterial tissue, including key constituents believed to be associated with vulnerable plaque such as lipid content.

Another method of locating vulnerable plaque is to use intravascular ultrasound (IVUS) to detect the shape of the arterial tissue surrounding the lumen. To use this method, one also inserts a catheter through the lumen of the artery. The catheter includes an ultrasound transducer to send ultrasound energy towards the arterial wall. The reflected ultrasound energy is received by the ultrasound transducer and is used to map the shape of the arterial tissue. This map of the morphology of the arterial wall can be used to detect the fibrous cap associated with vulnerable plaque.

SUMMARY

The invention is based on the recognition that combining two detection modalities, infrared spectroscopy and IVUS, in the same probe increases the probe's ability to detect lesions such as vulnerable plaque.

In one aspect, the invention includes an intravascular probe having a sheath with a distal portion and a proximal portion. The intravascular probe includes a first optical waveguide extending along the sheath, the first optical waveguide being configured to carry optical radiation between the distal and proximal portions, and a first beam redirector disposed at the distal portion in optical communication with the first optical waveguide. The intravascular probe also includes an optical detector configured to receive optical radiation from the first optical waveguide, and an ultrasound transducer disposed at the distal portion. The ultrasound transducer is configured to couple ultrasound energy between the intravascular probe and a transmission medium. A wire extends along the sheath in electrical communication with the ultrasound transducer.

In some embodiments, the intravascular probe includes a second optical waveguide extending along the sheath. The second optical waveguide is configured to carry optical radiation between the distal and proximal portions. Embodiments of this type also include a second beam redirector disposed at the distal portion in optical communication with the second optical waveguide.

In some embodiments, the second beam redirector is configured to redirect an axially directed beam of optical radiation incident thereon from the second optical waveguide into a beam propagating along a direction having a radial component.

In another embodiment, the intravascular probe includes an optical source configured to couple optical radiation into the second optical waveguide.

In another aspect, the invention includes an intravascular probe having a sheath with a distal portion and a proximal portion. The intravascular probe includes a first optical waveguide extending along the sheath, the first optical waveguide being configured to carry optical radiation between the distal and proximal portions, and a first beam redirector disposed at the distal portion in optical communication with the first optical waveguide. The intravascular probe also includes a second optical waveguide extending along the sheath, the second optical waveguide being configured to carry optical radiation between the distal and proximal portions, and a second beam redirector disposed at the distal portion in optical communication with the second optical waveguide. The intravascular probe also includes an ultrasound transducer disposed at the distal portion. The ultrasound transducer is configured to couple ultrasound energy between the intravascular probe and a transmission medium. A wire extending along the sheath in electrical communication with the ultrasound transducer. An example of an optical waveguide is an optical fiber.

In one embodiment, the intravascular probe also includes an optical detector configured to receive optical radiation from the first optical waveguide.

In another embodiment, the intravascular probe includes an optical source configured to couple optical radiation into the first optical waveguide. The optical source can be configured to emit infrared radiation.

In one embodiment, the first beam redirector includes an optical reflector. However, the first beam redirector can also include a prism or a bend in a distal tip of the first optical waveguide.

In another embodiment, the ultrasound transducer includes a piezoelectric transducer.

In another embodiment, the sheath includes a material that is transparent to infrared radiation.

In some embodiments, the first beam redirector is rigidly connected to the ultrasound transducer. In other embodiments, the first beam redirector is flexibly connected to the ultrasound transducer.

In some embodiments, the first beam redirector is configured to emit light from a first axial location with respect to a longitudinal axis of the sheath, and the ultrasound transducer is configured to emit ultrasound energy from the first axial location. In other embodiments, the first beam redirector is configured to emit light from a first axial location with respect to a longitudinal axis of the sheath, and the ultrasound transducer is configured to emit ultrasound energy from a second axial location different from the first axial location.

In some embodiments, the intravascular probe includes a rotatable cable surrounding the first optical waveguide and the wire, the rotatable cable being configured to coaxially rotate the first beam director and the ultrasound transducer. In other embodiments, the intravascular probe includes a plurality of beam redirectors circumferentially disposed about a longitudinal axis of the sheath, a plurality of optical waveguides in optical communication with the plurality of beam redirectors, and a plurality of ultrasound transducers circumferentially disposed about the longitudinal axis.

As used herein, "infrared" means infrared, near infrared, intermediate infrared, far infrared, or extreme infrared.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The vulnerability of a plaque to rupture can be assessed by detecting a combination of attributes such as macrophage presence, local temperature rise, and a lipid-rich pool covered by a thin fibrous cap. Some detection modalities are only suited to detecting one of these attributes.

Figure 1A:
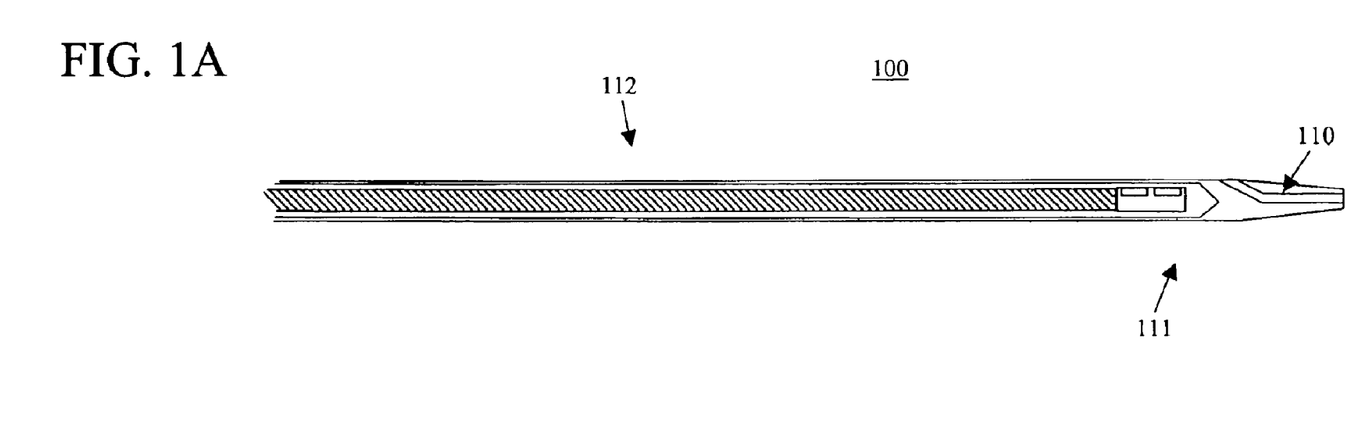
FIG. 1A is a cross-sectional view of an intravascular probe with an guidewire lumen in a distal end of a catheter.
Figure 1B:
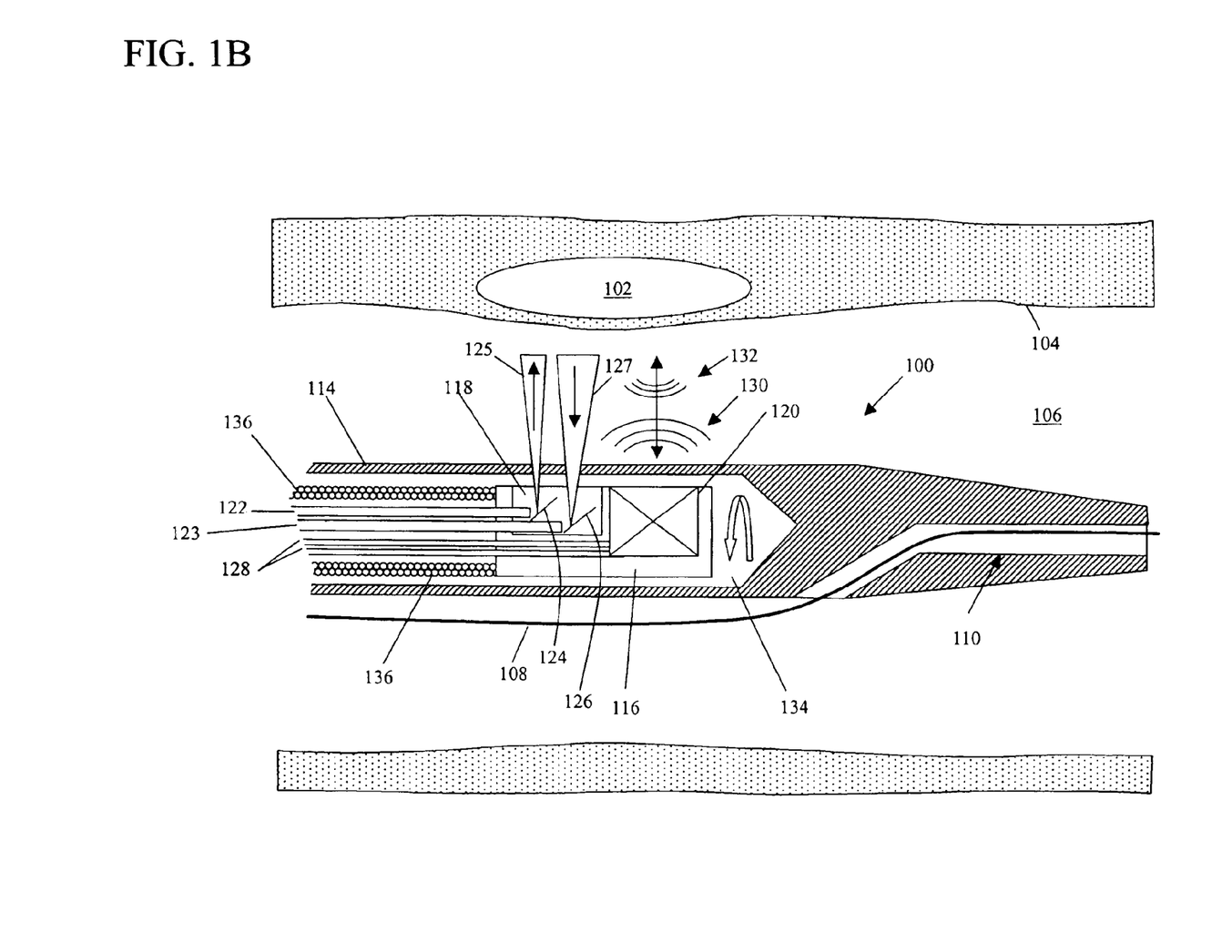
FIG. 1B is another cross-sectional view of the intravascular probe of FIG. 1A with a rotating core and a rigid coupling between an optical bench and an ultrasound transducer.

FIGS. 1A–1B show an embodiment of an intravascular probe 100 that combines two detection modalities for identifying vulnerable plaque 102 in an arterial wall 104 of a patient. The combination of both chemical analysis, using infrared spectroscopy to detect lipid content, and morphometric analysis, using IVUS to detect cap thickness, enables greater selectivity in identifying potentially vulnerable plaques than either detection modality alone. These two detection modalities can achieve high sensitivity even in an environment containing blood.

Referring to FIG. 1A, an intravascular probe 100 includes a catheter 112 with a guidewire lumen 110 at a distal end 111 of the catheter 112. Referring to FIG. 1B, the intravascular probe 100 can be inserted into a lumen 106 of an artery using a guidewire 108 that is threaded through the guidewire lumen 110. An outer layer of the catheter 112 is a sheath 114 is composed of a material that transmits infrared light (e.g., a polymer). A housing 116 is located at the distal end of the catheter 112 and includes an optical bench 118 to transmit and receive infrared light and an ultrasound transducer 120 to transmit and receive ultrasound energy. A delivery fiber 122 and a collection fiber 123 extend between proximal and distal ends of the catheter 112, and have distal ends seated in the optical bench 118. A light source (not shown) couples light into a proximal end of the delivery fiber 122, and a delivery mirror 124 redirects light 125 emitted from a distal end of the delivery fiber 122 towards the arterial wall 104. A collection mirror 126 redirects light 127 scattered from various depths of the arterial wall 104 into a distal end of the collection fiber 123. Other beam redirectors can be used in place of delivery mirror 124 and collection mirror 126 (e.g., a prism or a bend in the optical fiber tip). A proximal end of collection fiber 123 is in optical communication with an optical detector (not shown). The optical detector produces an electrical signal, indicative of the light intensity in the collection fiber 123, that contains a spectral signature indicating the composition of the arterial wall 104, and in particular, whether the composition is consistent with the presence of lipids found in a vulnerable plaque 102. The spectral signature in the electrical signal can be analyzed using a spectrum analyzer (not shown) implemented in hardware, software, or a combination thereof.

Figure 1C:
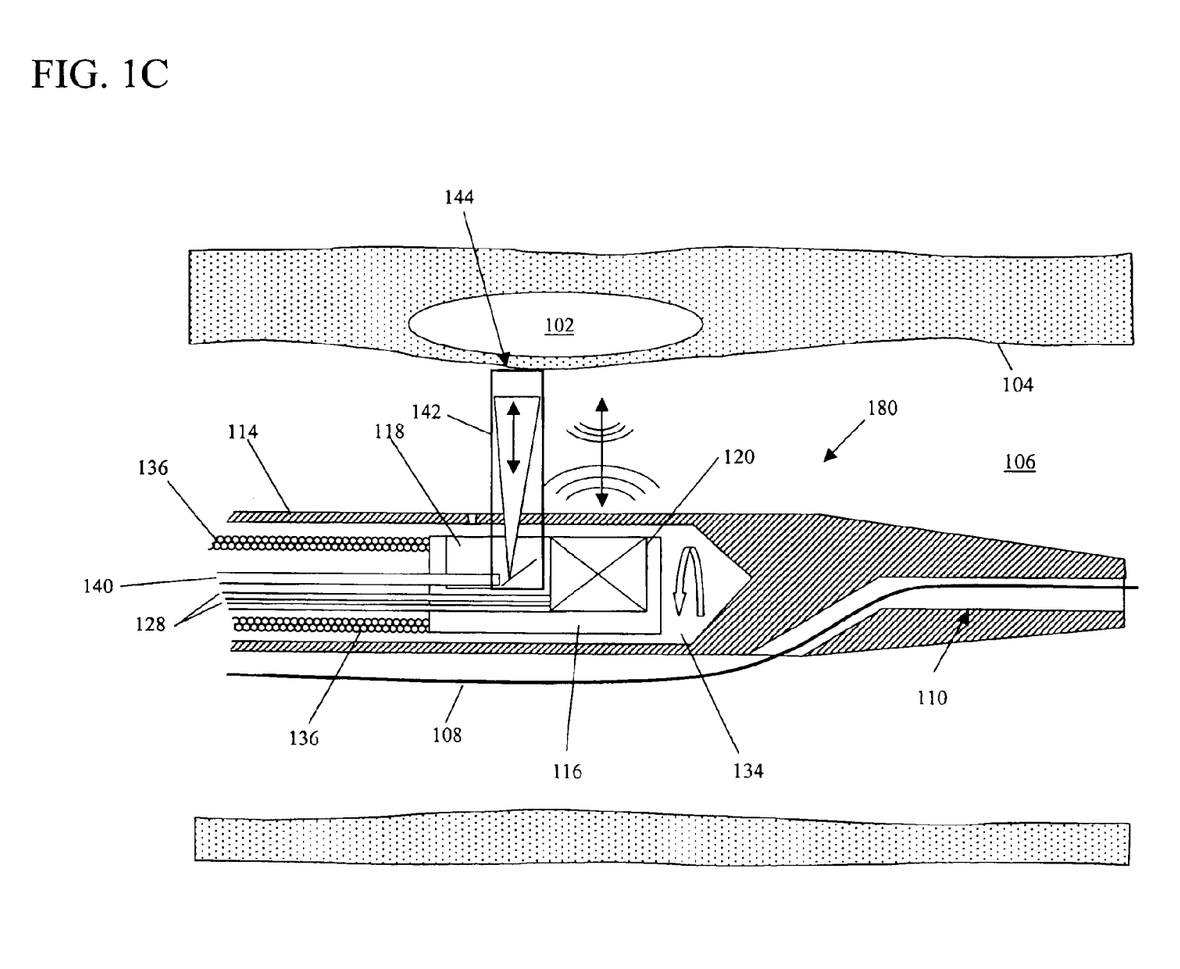
FIG. 1C is a cross-sectional view of an implementation of the intravascular probe of FIG. 1B with a single optical fiber.

Alternatively, in an implementation shown in FIG. 1C, an intravascular probe 180 can use a single optical fiber 140 in place of the delivery fiber 122 and the collection fiber 123. By collecting scattered light directly from the intraluminal wall 104, one avoids scattering that results from propagation of light through blood within the lumen 106. As a result, it is no longer necessary to provide separate collection and delivery fibers. Instead, a single fiber 140 can be used for both collection and delivery of light using an atraumatic light-coupler 142. Referring to FIG. 1C, the atraumatic light-coupler 142 rests on a contact area 144 on the arterial wall 104. When disposed as shown in FIG. 1C, the atraumatic light-coupler 142 directs light traveling axially on the fiber 140 to the contact area 144. After leaving the atraumatic light-coupler 142, this light crosses the arterial wall 104 and illuminates structures such as any plaque 102 behind the wall 104. These structures scatter some of the light back to the contact area 144, where it re-emerges through the arterial wall 104. The atraumatic light-coupler 142 collects this re-emergent light and directs it into the fiber 140. The proximal end of the optical fiber 144 can be coupled to both a light source and an optical detector (e.g., using an optical circulator).

The ultrasound transducer 120, which is longitudinally adjacent to the optical bench 118, directs ultrasound energy 130 towards the arterial wall 104, and receives ultrasound energy 132 reflected from the arterial wall 104. Using time multiplexing, the ultrasound transducer 120 can couple both the transmitted 130 and received 132 ultrasound energy to an electrical signal carried on wires 128. For example, during a first time interval, an electrical signal carried on wires 128 can actuate the ultrasound transducer 120 to emit a corresponding ultrasound signal. Then during a second time interval, after the ultrasound signal has reflected from the arterial wall, the ultrasound transducer 120 produces an electrical signal carried on wires 128. This electrical signal corresponds to the received ultrasound signal. The received electrical signal can be used to reconstruct the shape of the arterial wall, including cap thickness of any plaque 102 detected therein.

Inside the sheath 114 is a transmission medium 134, such as saline or other fluid, surrounding the ultrasound transducer 120 for improved acoustic transmission. The transmission medium 134 is also transparent to the infrared light emitted from the optical bench 118.

A torque cable 136 attached to the housing 116 surrounds the optical fibers 122 and the wires 128. A motor (not shown) rotates the torque cable 136, thereby causing the housing 116 to rotate. This feature enables the intravascular probe 100 to circumferentially scan the arterial wall 104 with light 124 and ultrasound energy 130.

During operation the intravascular probe 100 is inserted along a blood vessel, typically an artery, using the guidewire 108. In one practice the intravascular probe 100 is inserted in discrete steps with a complete rotation occurring at each such step. In this case, the optical and ultrasound data can be collected along discrete circular paths. Alternatively, the intravascular probe 100 is inserted continuously, with axial translation and rotation occurring simultaneously. In this case, the optical and ultrasound data are collected along continuous helical paths. In either case, the collected optical data can be used to generate a three-dimensional spectral map of the arterial wall 104, and the collected ultrasound data can be used to generate a three-dimensional morphological map of the arterial wall 104. A correspondence is then made between the optical and ultrasound data based on the relative positions of the optical bench 118 and the ultrasound transducer 120. The collected data can be used in real-time to diagnose vulnerable plaques, or identify other lesion types which have properties that can be identified by these two detection modalities, as the intravascular probe 100 traverses an artery. The intravascular probe 100 can optionally include structures for carrying out other diagnostic or treatment modalities in addition to the infrared spectroscopy and IVUS diagnostic modalities.

Figure 2:
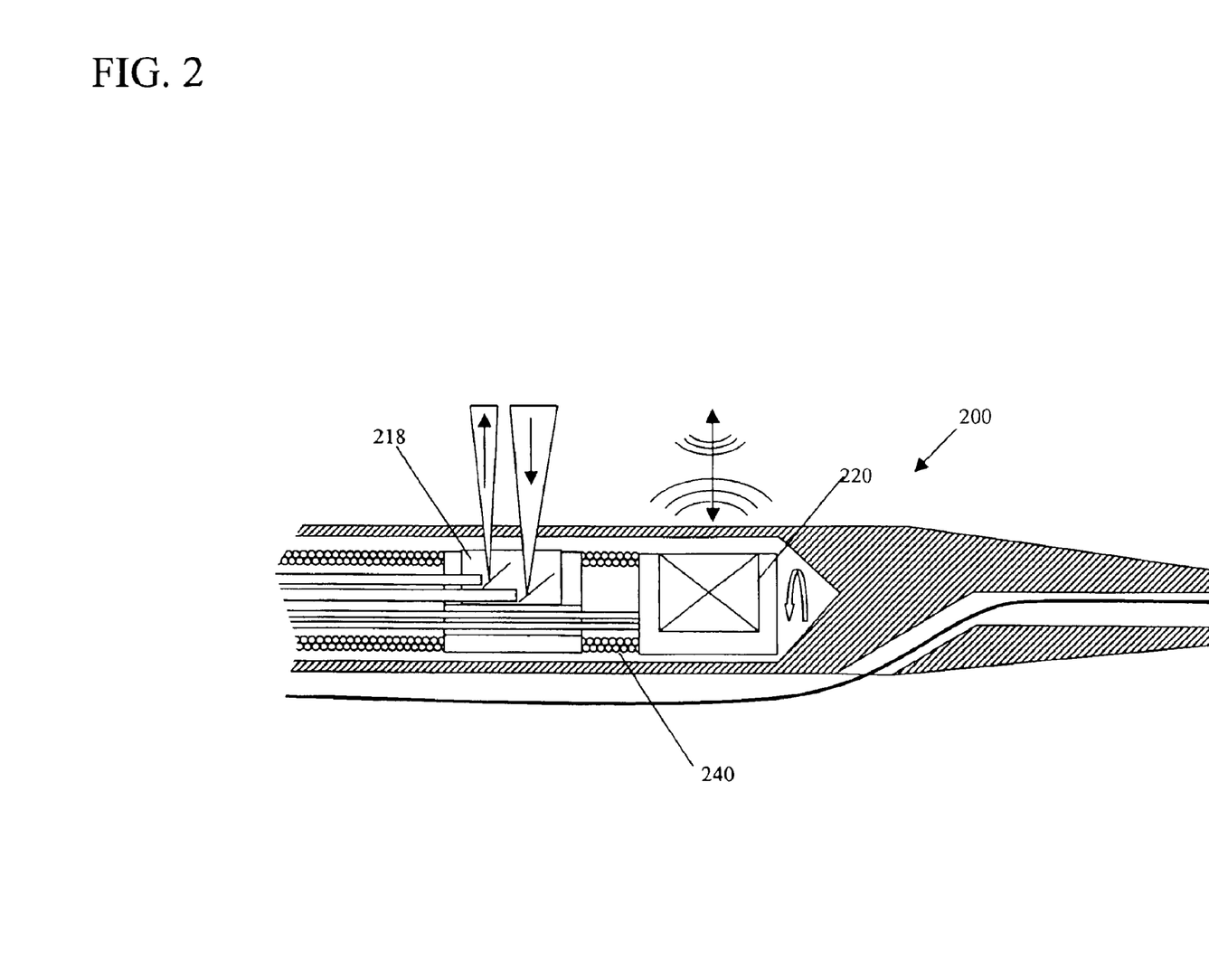
FIG. 2 is a cross-sectional view of an intravascular probe with a rotating core and a flexible coupling between an optical bench and ultrasound transducer.

FIG. 2 is a cross-sectional view of a second embodiment of an intravascular probe 200 in which a flexible coupling 240 links an optical bench 218 and an ultrasound transducer 220. When a catheter is inserted along a blood vessel, it may be beneficial to keep any rigid components as short as possible to increase the ability of the catheter to conform to the shape of the blood vessel. Intravascular probe 200 has the advantage of being able to flex between the optical bench 218 and the ultrasound transducer 220, thereby enabling the intravascular probe 200 to negotiate a tortuous path through the vasculature. However, the optical and ultrasound data collected from intravascular probe 200 may not correspond as closely to one another as do the optical and ultrasound data collected from the intravascular probe 100. One reason for this is that the optical bench 218 and the ultrasound transducer 220 are further apart than they are in the first embodiment of the intravascular probe 100. Therefore, they collect data along different helical paths. If the catheter insertion rate is known, one may account for this path difference when determining a correspondence between the optical and ultrasound data; however, the flexible coupling 240 between the optical bench 218 and the ultrasound transducer 220 may make this more difficult than it would be in the case of the embodiment in FIG. 1A.

Figure 3A:
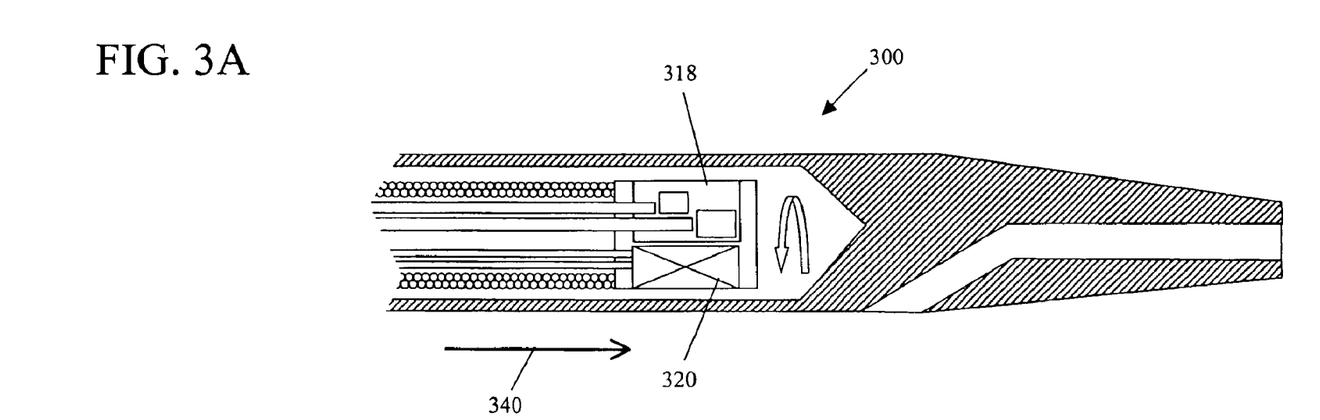
FIGS. 3A–B show top and side cross-sectional views of laterally adjacent unidirectional optical bench and ultrasound transducer in an intravascular probe with a rotating core.
Figure 3B:
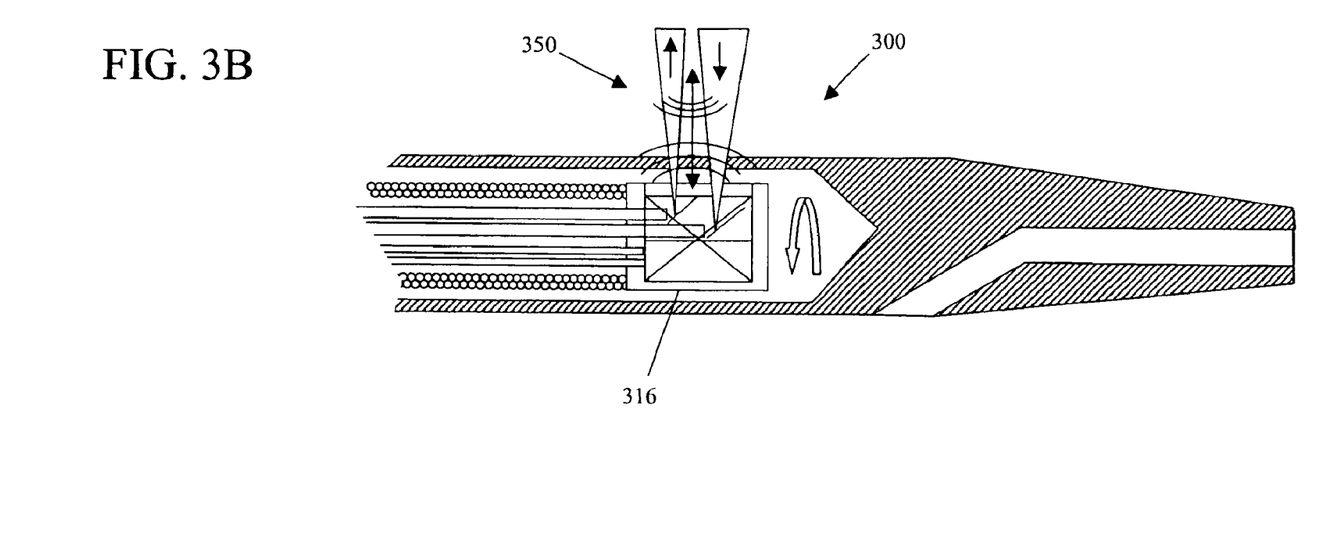

FIGS. 3A and 3B show cross-sectional views of a third embodiment in which the intravascular probe 300 has an optical bench 318 and an ultrasound transducer 320 that are laterally adjacent such that they emit light and ultrasound energy, respectively, from the same axial location with respect to a longitudinal axis 340 of the sheath 314. FIG. 3A shows the top view of the emitting ends of the optical bench 318 and ultrasound transducer 320. FIG. 3B is a side view showing the light and ultrasound energy emitted from the same axial location, so that as the housing 316 is simultaneously rotated and translated, the light and ultrasound energy 350 trace out substantially the same helical path. This facilitates matching collected optical and ultrasound data. A time offset between the optical and ultrasound data can be determined from the known rotation rate.

Figure 4:
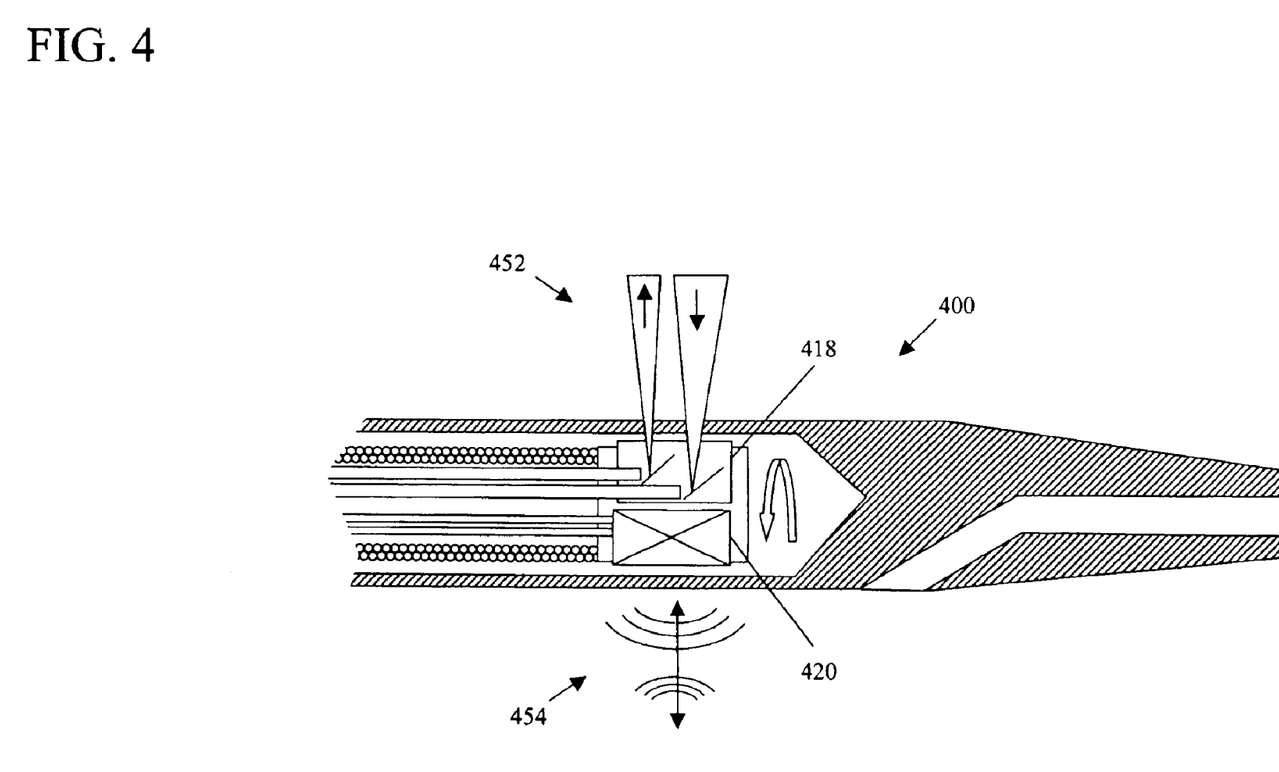
FIG. 4 is a cross-sectional view of an intravascular probe with a rotating core and laterally adjacent opposing optical bench and ultrasound transducer.

FIG. 4 is a cross-sectional view of a fourth embodiment in which intravascular probe 400 has a laterally adjacent and opposing optical bench 418 and ultrasound transducer 420 as described in connection with FIGS. 3A and 3B. However, in this embodiment, light 452 is emitted on one side and ultrasound energy 454 is emitted on an opposite side. This arrangement may allow intravascular probe 400 to have a smaller diameter than intravascular probe 300, depending on the geometries of the optical bench 418 and ultrasound transducer 420. A smaller diameter could allow an intravascular probe to traverse smaller blood vessels.

Figure 5:
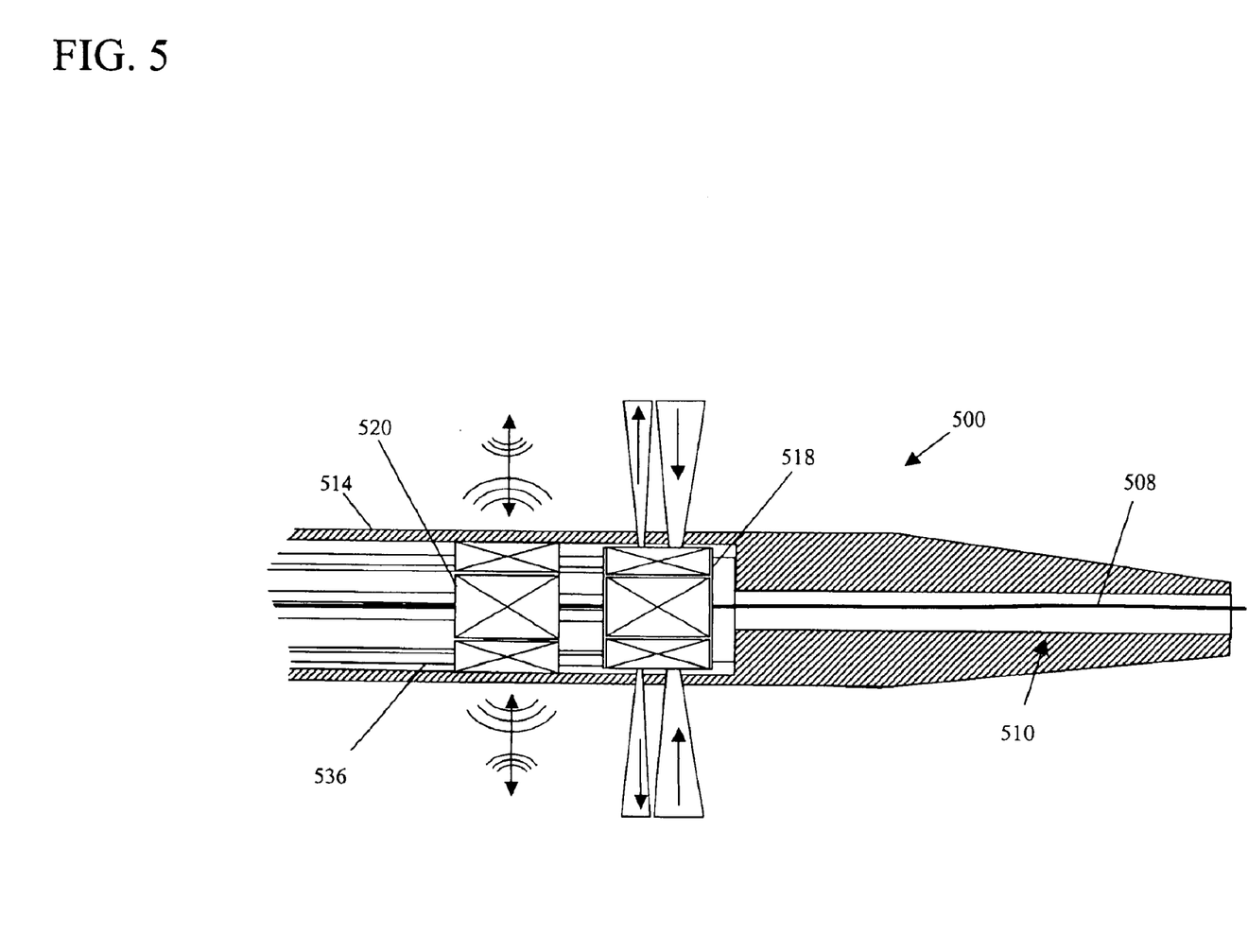
FIG. 5 is a cross-sectional view of an intravascular probe with a fixed core, an optical bench with a radial array of optical fibers, and a radial array of ultrasound transducers.

FIG. 5 is a cross-sectional view of a fifth embodiment in which intravascular probe 500 has a fixed core 536, a radial array of optical couplers 518, and a radial array of ultrasound transducers 520. The fifth embodiment, with its fixed core 536, is potentially more reliable than previous embodiments, with their rotating cores. This is because the fifth embodiment lacks moving parts such as a torque cable. Lack of moving parts also makes intravascular probe 500 safer because, should the sheath 514 rupture, the arterial wall will not contact moving parts.

The intravascular probe 500 can collect data simultaneously in all radial directions thereby enhancing speed of diagnosis. Or, the intravascular probe 500 can collect data from different locations at different times, to reduce potential crosstalk due to light being collected by neighboring optical fibers or ultrasound energy being collected by neighboring transducers. The radial resolution of spectral and/or morphological maps will be lower than the maps created in the embodiments with rotating cores, although the extent of this difference in resolution will depend on the number of optical fibers and ultrasound transducers. A large number of optical fibers and/or ultrasound transducers, while increasing the radial resolution, could also make the intravascular probe 500 too large to fit in some blood vessels.

Intravascular probe 500 can be inserted through a blood vessel along a guidewire 508 that passes through a concentric guidewire lumen 510. Inserting a catheter using a concentric guidewire lumen 510 has advantages over using an off-axis distal guidewire lumen 110. One advantage is that the guidewire 508 has a smaller chance of becoming tangled. Another advantage is that, since a user supplies a load that is coaxial to the wire during insertion, the concentric guidewire lumen 510 provides better trackability. The concentric guidewire lumen 510 also removes the guidewire 508 from the field of view of the optical fibers and ultrasound transducers.

Figure 6A:
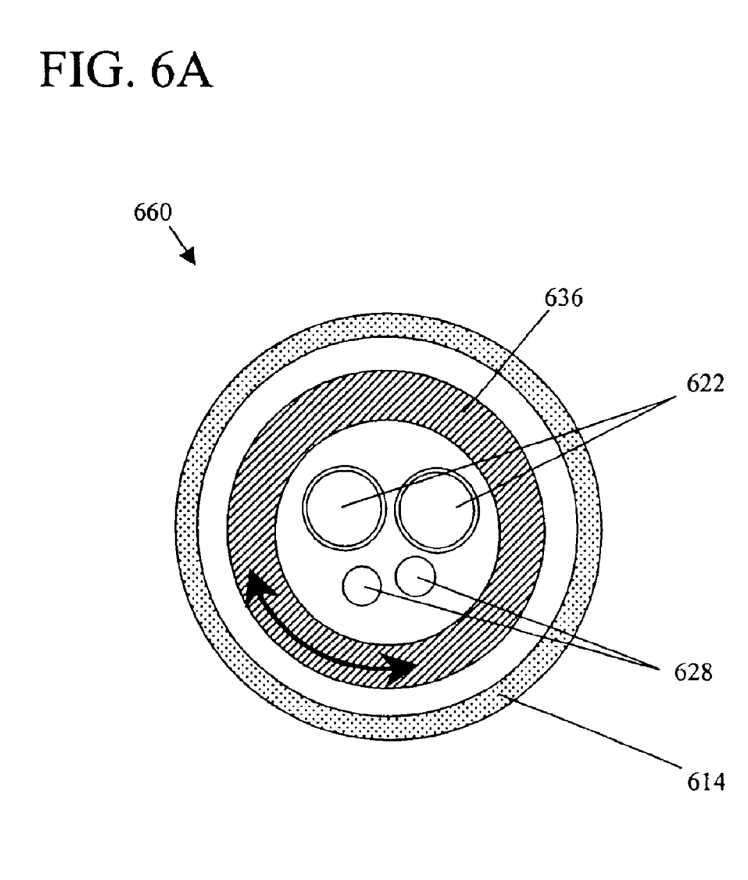
FIGS. 6A–B compare transverse cross-sectional views of catheters with rotating and fixed cores.
Figure 6B:
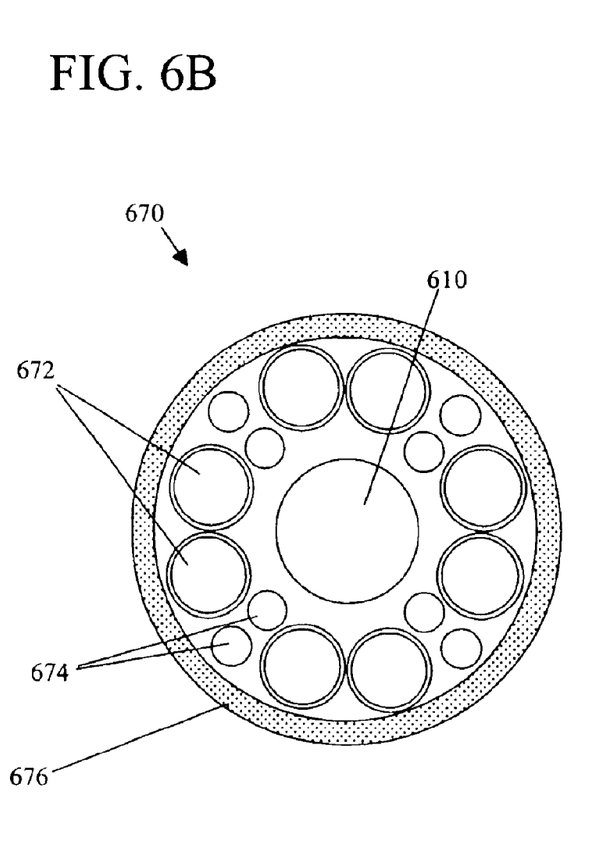

The intravascular probes include a catheter having a diameter small enough to allow insertion of the probe into small blood vessels. FIGS. 6A and 6B compare transverse cross-sectional views of catheters from embodiments with rotating cores (FIGS. 1–4) and fixed cores (FIG. 5).

The rotating core catheter 660, shown in FIG. 6A, includes a single pair of optical fibers 622, for carrying optical signals for infrared spectroscopy, and a single pair of wires 628, for carrying electrical signals for IVUS, within a hollow torque cable 636. The diameter of the sheath 614 of catheter 660 is limited by the size of the torque cable 636.

The fixed core catheter 670, shown in FIG. 6B, has four optical fiber pairs 672, and four wire pairs 674, for carrying optical signals and electrical IVUS signals, respectively, from four quadrants of the arterial wall. While no torque cable is necessary, the sheath 676 of catheter 670 should have a diameter large enough to accommodate a pair of optical fibers 672 and a pair of wires 674 for each of the four quadrants, as well as a concentric guidewire lumen 610.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An intravascular probe comprising:
   a sheath having a distal portion and a proximal portion;
   a first optical waveguide extending along the sheath, the first optical waveguide being configured to carry optical radiation between the distal and proximal portions;
   an optical bench disposed at the distal portion, in which a distal end of the first optical waveguide is seated;
   a first beam redirector disposed on the optical bench in optical communication with the first optical waveguide;
   an optical detector configured to receive optical radiation from the first optical waveguide;
   an ultrasound transducer disposed at the distal portion and coupled to the optical bench, the ultrasound transducer being configured to couple ultrasound energy between the intravascular probe and a transmission medium; and
   a wire extending along the sheath in electrical communication with the ultrasound transducer.

2. The intravascular probe of claim 1, further comprising:
   a second optical waveguide extending along the sheath, the second optical waveguide being configured to carry optical radiation between the distal and proximal portions, and having a distal end seated in the optical bench;
   a second beam redirector disposed on the optical bench in optical communication with the second optical waveguide.

3. The intravascular probe of claim 2, wherein the second beam redirector is configured to redirect an axially directed beam of optical radiation incident thereon from the second optical waveguide into a beam propagating along a direction having a radial component.

4. The intravascular probe of claim 2, further comprising an optical source configured to couple optical radiation into the second optical waveguide.

5. The intravascular probe of claim 1, further comprising a rotatable cable surrounding the first optical waveguide and the wire, the rotatable cable being configured to coaxially rotate the first beam redirector and the ultrasound transducer.

6. The intravascular probe of claim 5, wherein the optical bench is disposed beyond a distal end of the cable.

7. The intravascular probe of claim 1, wherein the ultrasound transducer is rigidly coupled to the optical bench.

8. The intravascular probe of claim 1, wherein the ultrasound transducer is flexibly coupled to the optical bench.

9. An intravascular probe comprising:
   a sheath having a distal portion and a proximal portion;
   a first optical waveguide extending along the sheath, the first optical waveguide being configured to carry optical radiation between the distal and proximal portions;
   an optical bench disposed at the distal portion, in which a distal end of the first optical waveguide is seated;
   a first beam redirector disposed on the optical bench in optical communication with the first optical waveguide;
   a second optical waveguide extending along the sheath, the second optical waveguide being configured to carry optical radiation between the distal and proximal portions, and having a distal end seated in the optical bench;
   a second beam redirector disposed on the optical bench in optical communication with the second optical waveguide;
   an ultrasound transducer disposed at the distal portion and coupled to the optical bench, the ultrasound transducer being configured to couple ultrasound energy between the intravascular probe and a transmission medium; and
   a wire extending along the sheath in electrical communication with the ultrasound transducer.

10. The intravascular probe of claim 9, wherein the first beam redirector is configured to redirect an axially directed beam of optical radiation incident thereon from the first optical waveguide into a beam propagating along a direction having a radial component.

11. The intravascular probe of claim 9, further comprising an optical detector configured to receive optical radiation from the first optical waveguide.

12. The intravascular probe of claim 9, further comprising an optical source configured to couple optical radiation into the first optical waveguide.

13. The intravascular probe of claim 12, wherein the optical source is configured to emit infrared radiation.

14. The intravascular probe of claim 9, wherein the first optical waveguide comprises an optical fiber.

15. The intravascular probe of claim 9, wherein the first beam redirector comprises an optical reflector.

16. The intravascular probe of claim 9, wherein the first beam redirector comprises a prism.

17. The intravascular probe of claim 9, wherein the first redirector comprises a bend in a distal tip of the first optical waveguide.

18. The intravascular probe of claim 9, wherein the ultrasound transducer comprises a piezoelectric transducer.

19. The intravascular probe of claim 9, wherein the sheath comprises a material that is transparent to infrared radiation.

20. The intravascular probe of claim 9, wherein the first beam redirector is rigidly connected to the ultrasound transducer.

21. The intravascular probe of claim 9, wherein the first beam redirector is flexibly connected to the ultrasound transducer.

22. The intravascular probe of claim 9, wherein the first beam redirector is configured to emit light from a first axial location with respect to a longitudinal axis of the sheath, and the ultrasound transducer is configured to emit ultrasound energy from the first axial location.

23. The intravascular probe of claim 9, wherein the first beam redirector is configured to emit light from a first axial location with respect to a longitudinal axis of the sheath, and the ultrasound transducer is configured to emit ultrasound energy from a second axial location different from the first axial location.

24. The intravascular probe of claim 9, further comprising a rotatable cable surrounding the first optical waveguide and the wire, the rotatable cable being configured to coaxially rotate the first beam redirector and the ultrasound transducer.

25. The intravascular probe of claim 24, wherein the optical bench is disposed beyond a distal end of the cable.

26. The intravascular probe of claim 9, further comprising:

a plurality of beam redirectors circumferentially disposed about a longitudinal axis of the sheath;

a plurality of optical waveguides in optical communication with the plurality of beam redirectors; and a plurality of ultrasound transducers circumferentially disposed about the longitudinal axis.

27. The intravascular probe of claim 9, wherein the ultrasound transducer is rigidly coupled to the optical bench.

28. The intravascular probe of claim 9, wherein the ultrasound transducer is flexibly coupled to the optical bench.

* * * * *